United States Patent
Ricca (10) Patent No.: US 6,660,285 B2
(45) Date of Patent: Dec. 9, 2003

(54) USE OF AMPHOTERIC SURFACTANTS IN COSMETIC COMPOSITIONS TO PRECIPITATE CATIONIC POLYMERS ON DILUTION

(76) Inventor: Jean-Marc Ricca, 16, Avenue Michel Bizot, Paris (FR), F-75012

( * ) Notice: Subject to any disclaimer, the term of this patent is extended or adjusted under 35 U.S.C. 154(b) by 155 days.

(21) Appl. No.: 10/188,896

(22) Filed: Jul. 5, 2002

(65) Prior Publication Data

US 2003/0086953 A1 May 8, 2003

Related U.S. Application Data

(62) Division of application No. 09/600,371, filed as application No. PCT/FR99/00073 on Jan. 15, 1999, now Pat. No. 6,475,474.

(30) Foreign Application Priority Data

Jan. 19, 1998 (FR) ............................................. 98 00634

(51) Int. Cl.[7] .............................. A61K 7/00; A61K 7/06; A61K 7/075; A61K 7/08
(52) U.S. Cl. ................... 424/401; 424/70.1; 424/70.19; 424/70.21; 424/70.22; 424/70.24; 424/400
(58) Field of Search ................................ 424/400, 401, 424/70.1, 70.19, 70.21, 70.22, 70.24

(56) References Cited

U.S. PATENT DOCUMENTS 6,210,689 B1 * 4/2001 Martino et al. ............. 424/401

FOREIGN PATENT DOCUMENTS

| WO | 9637591 | 11/1996 |
| WO | 9704743 | 2/1997 |

* cited by examiner

*Primary Examiner*—Shelley A. Dodson
(74) *Attorney, Agent, or Firm*—Stevens, Davis, Miller & Mosher, LLP (57) ABSTRACT

The invention relates to the use of at least one amphoteric in transparent aqueous cosmetic compositions for the hair and/or the skin designed to be rinsed, comprising at least one anionic surface-active agent, at least one surface-active agent selected for the betaines and at least one water-soluble or water dispersible cationic polymer derived from a polysaccharide (PolC), as precipitant, in the diluted state, of said cationic polymer (PolC). The invention further relates to transparent aqueous cosmetic compositions for the hair and/or skin designed to be rinsed, comprising at least one one anionic surface-active agent, at least one surface-active agent selected for the betaines, at least one water-soluble or water dispersible cationic polymer derived from a polysaccharide (PolC), and at least one amphoteric surface-active agent.

13 Claims, 3 Drawing Sheets

USE OF AMPHOTERIC SURFACTANTS IN COSMETIC COMPOSITIONS TO PRECIPITATE CATIONIC POLYMERS ON DILUTION

This application is a divisional of U.S. application Ser. No. 09/600,371, filed on Jul. 14, 2000 now U.S. Pat. No. 6,475,474, incorporated herein by reference, which is an application under 35 U.S.C. Section 371 of International Application Number PCT/FR99/00073 filed on Jan. 15, 1999.

BACKGROUND OF THE INVENTION

1. Field of the Invention

The present invention relates to the use, in transparent aqueous cosmetic compositions for rinsing, of at least one amphoteric surfactant as an agent for precipitating hydrosoluble or hydrodispersible cationic polymers derived from polysaccharides (in particular cationic celluloses and hydroxyalkylated cationic guars) included in said compositions, on dilution during application of said compositions to the hair and/or the skin; it also relates to aqueous cosmetic compositions for the hair and/or the skin comprising, in addition to said amphoteric surfactant, at least one anionic surfactant, at least one surfactant selected from betaines and at least one hydrosoluble cationic polymer derived from a polysaccharide.

2. Background

Human hair or skin becomes dirty on contact with atmospheric pollution and to a greater extent with natural secretions such as sebum. This phenomenon necessitates cleaning the skin and hair frequently using cosmetic compositions. While their detergent properties are usually largely satisfactory, frequent and repeated washing often leaves the hair in a condition which requires a complementary treatment. Different solutions have been proposed to overcome this problem, from using conditioning agents included in the cosmetic formulation to developing specific products used in a post treatment.

For cost and effectiveness reasons, it is desirable to maximise the deposit of conditioning agents on the hair and/or skin. A general approach consists of using associative interactions between an anionic surfactant and a cationic polymer, which interactions lead to precipitation of a surfactant/polymer complex on the desired surface. Examples which can be cited are formulations based on the sodium lauryl ether sulphate/cocamidopropylbetaine and guar hydroxypropyl trimonium chloride system such as Jaguar C13S sold by Rhone-Poulenc. That system precipitates on dilution by phase separation, leading to an increased deposit of the polymer on the surface of the hair and/or skin. However, that system cannot produce formulations with the desired transparency.

One solution for improving transparency consists of using hydroxypropyl guar hydroxypropyl trimonium chloride such as JAGUAR C162 sold by Rhone-Poulenc, but the system formed by association with the surfactants cited above do not precipitate on dilution.

SUMMARY OF THE INVENTION

The Applicant has unexpectedly discovered that addition of a small quantity of an amphoteric type surfactant to an aqueous transparent medium containing an anionic surfactant, a surfactant of the betaine type and a hydrosoluble or hydrodispersible cationic polymer derived from a polysaccharide which does not precipitate out on dilution by phase separation (cationic celluloses and hydroxyalkylated cationic guars in particular) can, on dilution, precipitate said cationic polymer by a phase separation phenomenon.

For cosmetic applications, this precipitation causes a substantial increase in the deposit of the cationic polymer derived from a polysaccharide on the hair and/or skin, when said aqueous medium is diluted by contact with the damp and/or wet hair and/or skin.

This system can also be used to simultaneously increase the deposit of non hydrosoluble organic cosmetic agents which can be present in the form of dispersions of particles.

DETAILED DESCRIPTION OF THE PREFERRED EMBODIMENTS

In a first aspect, the present invention concerns the use, in transparent aqueous cosmetic compositions for the hair and/or skin intended to be rinsed, of at least one amphoteric surfactant (A) in a quantity of the order of 0.5% to 10% by weight, preferably of the order of 0.5% to 3% by weight with respect to the weight of same cosmetic compositions, as an agent for precipitating a hydrosoluble or hydrodispersible cationic polymer derived from a polysaccharide (PolC) on dilution during application of said compositions to the hair and/or skin; at least 90% of the weight of said transparent aqueous cosmetic compositions being comprised by an aqueous phase (Φ) with 8% to 20% of its weight being comprised by a system (S) formed by at least one anionic surfactant (TAn), at least one surfactant selected from betaines (TB) and at least one hydrosoluble or hydrodispersible cationic polymer derived from a polysaccharide (PolC); the respective quantities of constituents (TAn), (TB) and (PolC) and the nature of the cationic polymer (PolC) in said system (S) being such that the transmittance of the aqueous phase (Φ) constituted by said system (S) in aqueous solution in a concentration of 8% to 20%, measured at 600 nanometres, is at least 90% and that it does not phase separate with formation of a precipitate on dilution.

In accordance with the invention, the aqueous phase (Φ) of said system (S) in aqueous solution in a concentration of 8% to 20% does not phase separate with formation of a precipitate on dilution, this same aqueous phase (Φ) exhibiting phase separation with formation of a precipitate on dilution in the presence of an amphoteric surfactant (A).

This phenomenon of phase separation on dilution occurs or is manifested during use of said cosmetic composition on contact with the surface to be treated (hair and/or skin), which surface already has a relatively high degree of hydration (for example wet or damp hair).

In the case of a shampoo, for example, the dilution factor of the cosmetic composition during application can be evaluated to a value of the order of 3 to 10, assuming that one gram of wet hair retains an average of 0.6 to 1 g of water, and that conventionally, 0.1 g of shampoo is applied per gram of dry hair, with an application duration of 30 to 45 seconds in general.

After having been applied, the cosmetic composition must then be rinsed to eliminate excess surfactants.

To implement the invention properly, said aqueous phase (Φ) comprises:

of the order of 5% to 15% of its weight, preferably of the order of 8% to 12% of its weight, of at least one anionic surfactant (TAn);

of the order of 0.5% to 10% of its weight, preferably of the order of 0.5% to 3% of its weight, of at least one surfactant selected from betaines (TB);

and of the order of 0.015% to 2% of its weight, preferably of the order of 0.05% to 0.5% of its weight, of at least one cationic polymer (PolC).

Cationic polymers (PolC) which do not precipitate on dilution of the aqueous phase (Φ) in the absence of an amphoteric surfactant (A), but which in the presence of an amphoteric surfactant (A) do exhibit phase separation behaviour with formation of a precipitate include cationic derivatives of cellulose and hydroxyalkylated cationic guar derivatives.

Preferred cationic polymers which can be mentioned are hydroxyalkylated ($C_2$–$C_{22}$) derivatives of cationic guars such as hydroxypropyl guar hydroxypropyl trimonium chloride (JAGUAR C162 and JAGUAR C2000 sold by Rhone-Poulenc) and cationic cellulose derivatives, in particular cellulose,2-(2-hydroxy-3-(trimethylammonium)propoxy) ethyl ether,chloride or polyquaternium-10 (polymer JR400 sold by Union Carbide).

The cationic nature of these polymers is variable: thus in the case of cationic hydroxypropylated guar derivatives such as JAGUAR C162 and C2000 sold by Rhone-Poulenc, the degree of hydroxypropylation (molar substitution, MS), is in the range 0.02 to 1.2 and the degree of substitution, DS is in the range 0.01 to 0.6. These products can optionally be functionalised by hydrophobic groups such as alkyl chains.

These cationic polymers can optionally be functionalised by anionic groups such as carboxymethyl, sulphate, sulphonate or phosphate, provided that the degree of substitution of these anionic groups is always less than the degree of substitution of the cationic groups.

The molecular weight of these cationic polymers is generally at least 2000, more generally of the order of 200000 to 3000000.

Anionic surfactants (TAn) which can be present in the context of the present invention which can be cited include:

alkylester sulphonates with formula R—CH($SO_3$M)—COOR', where R represents a $C_8$–$C_{20}$ alkyl radical, preferably $C_{10}$–$C_{16}$, R' represents a $C_1$–$C_6$ alkyl radical, preferably $C_1$–$C_3$, and M represents an alkali cation (sodium, potassium, lithium), substituted or non substituted ammonium (methyl-, dimethyl-, trimethyl-, tetramethyl-ammonium, dimethylpiperidinium,,) or an alkanolamine derivative (monoethanolamine, diethanolamine, triethanolamine . . . ). More particularly, methyl ester sulphonates where radical R is $C_{14}$–$C_{16}$ can be cited;

alkylsulphates with formula ROSO$_3$M, where R represents an alkyl or hydroxyalkyl $C_{10}$–$C_{24}$ radical, preferably $C_{12}$–$C_{20}$ and more particularly $C_{12}$–$C_{18}$, M representing a hydrogen atom or a cation with the same definition as that given above, and their ethoxylenated (OE) and/or propoxylenated (OP) derivatives, with an average of 0.5 to 6, preferably 0.5 to 3 OE and/or OP motifs;

alkylamide sulphates with formula RCONHR'OSO$_3$M, where R represents a $C_2$–$C_{22}$ alkyl radical, preferably $C_6$–$C_{20}$, R' represents a $C_2$–$C_3$ alkyl radical, M represents a hydrogen atom or a cation with the same definition as above, and their ethoxylenated (OE) and/or propoxylenated (OP) derivatives, with an average of 0.5 to 60 OE and/or OP motifs;

salts of saturated or unsaturated $C_8$–$C_{24}$ fatty acids, preferably $C_{14}$–$C_{20}$, $C_9$–$C_{20}$ alkylbenzenesulphonates, primary or secondary $C_8$–$C_{22}$ alkylsulphonates, alkylglycerol sulphonates, sulphonated polycarboxylic acids described in United Kingdom patent GB-A-1 082 179, paraffin sulphonates, N-acyl-N-alkyltaurates, alkylphosphates, alkylisethionates, alkylsuccinamates, alkylsulphosuccinates, sulphosuccinate monoesters or diesters, N-acyl sarcosinates, alkylglycoside sulphates, polyethoxycarboxylates;

The cation being an alkali metal (sodium, potassium, lithium), a substituted or non substituted ammonium residue (methyl-, dimethyl-, trimethyl-, tetramethylammonium, dimethylpiperidinium . . . ), or derived from an alkanolamine (monoethanolamine, diethanolamine, triethanolamine . . . );

Preferably, ethoxylated derivatives of fatty acids are used, in particular derivatives of lauric acid such as sodium or magnesium lauryl ether sulphate, or mixtures thereof.

The term "surfactant selected from betaines (TB)" means any surfactant carrying a permanent negative charge and positive charge on the same molecule whatever the pH and not having an isoelectric point. They are quaternised derivatives.

Examples which can be cited are:
betaines with formula:

such as lauryl betaine (Mirataine BB from Rhone-Poulenc);
sulphobetaines with formula:

amidoalkylbetaines with formula:

such as cocamidopropylbetaine (Mirataine BDJ from Rhone-Poulenc);
sulphobetaines with formula such as cocamidopropylhydroxysultaine (Mirataine CBS from Rhone-Poulenc), in which formula radicals $R^1$ represent an alkyl or alkenyl radical containing 10 to 24 carbon atoms, $R^2$, $R^3$, $R^4$ and $R^5$, which may be identical or different, represent an alkyl or alkylene radical containing 1 to 4 carbon atoms.

The term "amphoteric surfactant (A)" means any surfactant simultaneously carrying an anionic charge and a cationic charge, wherein the degree of ionisation varies as a function of the pH of the medium it is in. These products have an isoelectric point (IEP) in the range 3.5 to 6.5.

Examples which can be cited are:

alkyl or alkenyl-amphoacetates or ampho-diacetates, more generally with formula:

where $R^1$ represents an alkyl or alkenyl radical containing 10 to 24 carbon atoms, usually the coco and lauryl chains (Miranol C2M and Miranol Ultra C32 from Rhone-Poulenc), and X represents a hydrogen atom, an alkali metal or an alkaline-earth metal, or an amine;

alkylampho-propionates or -dipropionates (Miranol C2M SF from Rhone-Poulenc);

alkyl amphohydroxypropyl sultaines (Miranol CS from Rhone-Poulenc), the alkyl groups of which contain 8 to 24 carbon atoms, usually coco or lauryl.

In a variation, said amphoteric surfactant (A) can also be used to increase the deposit of particles of non hydrosoluble organic compounds (POins) of cosmetic interest, during dilution on use of said cosmetic compounds also containing at least one aqueous dispersion of said non hydrosoluble organic particles.

Said particles can be present in said compositions in an amount of the order of 0.1% to 10% by weight, preferably of the order of 0.2% to 2% by weight. The size can be in the range 0.15 to 70 microns.

Cosmetically interesting insoluble organic compounds (POins) which can be present in the form of particles in aqueous dispersion in said cosmetic compositions which can be mentioned include non hydrosoluble and non volatile organopolysiloxanes (also known as non hydrosoluble and non volatile silicones), among which can be cited oils, gums or polyalkylsiloxane resins, polyarylsiloxanes, polyalkylaryl siloxanes, or their non volatile functionalised non hydrosoluble derivatives, or mixtures thereof.

Said organopolysiloxanes are considered to be non hydrosoluble and non volatile when their solubility in water is less than 50 g/litre and their intrinsic viscosity is at least 3000 mPa.s at 25° C.

More particular examples of non hydrosoluble and non volatile organopolysiloxanes or silicones which can be cited are silicone gums such as diphenyldimethicone gum sold by Rhone-Poulenc, and preferably polydimethylsiloxanes with a viscosity of at least 600000 mPa.s at 25° C., more preferably those with a viscosity of more than 2000000 mPa.s at 25° C., such as Mirasil DM 500000® sold by Rhone-Poulenc.

The non hydrosoluble and non volatile organopolysiloxane or silicone is in the dispersed form in the cosmetic composition containing it. This is in the form of particles the size of which can be selected as a function of the nature of the cosmetic composition or the desired performance of the composition. In general, this size can be from 0.02 to 70 microns. Preferably, this size is of the order of 1 to 80 microns, more particularly of the order of 1 to 30 microns.

These silicone particles can be constituted by a mixture of silicones the presence of which may be due to the mode of use of the silicone agent of cosmetic interest in the cosmetic composition. Thus the cosmetically interesting organopolysiloxanes may be initially dispersed or dissolved in low viscosity silicone derivatives which may or may not be volatile, then emulsified in the cosmetic composition. Examples of low viscosity silicones which can be cited are cyclic volatile silicones and low mass polydimethylsiloxanes.

Functionalised silicone derivatives such as amine derivatives can also be mentioned as the polyorganosiloxanes, for example Mirasil ADM-E sold by Rhone-Poulenc (directly employed in the form of emulsions in the cosmetic composition or from preformed micro-emulsions).

Insoluble organic compounds which can be present in the form of particles which can also be mentioned include oils which can exert conditioning, protective or emollient functions; the oils are generally selected from alkylmonoglycerides, alkyldiglycerides, triglycerides such as oils extracted from plants and vegetables (palm oil, coprah oil, cottonseed oil, soyabean oil, sunflower seed oil, olive oil, grapeseed oil, sesame seed oil, peanut oil, castor oil . . . ) or oils of animal origin (tallow, fish oils . . . ), derivatives of these oils such as hydrogenated oils, lanolin derivatives, mineral oils or paraffin oils, perhydrosqualane, squalene, diols such as 1,2-dodecanediol, cetyl alcohol, stearyl alcohol, oleic alcohol, fatty esters such as isopropyl palmitate, 2-ethylhexyl cocoate, myristyl myristate, or lactic acid esters of stearic acid, behenic acid, isostearic acid.

Bactericidal or fungicidal agents to improve skin disinfection can also be mentioned, such as triclosan, anti-dandruff agents such as zinc pyrithone or octopyrox, or insecticidal agents such as natural or synthetic pyrethroids. These different organic molecules can if necessary be previously encapsulated in appropriate matrices using methods which are known in the art. An example which can be cited is encapsulation of organic molecules in polymer latexes.

The water-insoluble organic particles can also be constituted by agents for protecting the skin and/or hair against sun damage and UV damage, such as solar filters which are chemical compounds which strongly absorb UV radiation such as the compounds authorised in European Directive 76/768/EEC, its annexes and subsequent amendments.

In the case where the cosmetically interesting insoluble organic compounds have too high a micellar solubility (with respect to the quantity of surfactants present), or are in a form which is solid at ambient temperature, these can either be dissolved in an organic vehicle such as mineral or natural oils, silicone derivatives, waxes, or they can be encapsulated in matrices such as polymers (for example acrylics) present in dispersion, for example in the form of a latex.

In a second aspect, the invention provides transparent aqueous cosmetic compositions for the hair and/or skin intended to be rinsed, comprising at least 90% of their weight of an aqueous phase (Φ) comprising:

at least one amphoteric surfactant (A) in a quantity of the order of 0.5% to 10% by weight, preferably of the order of 0.5% to 3% by weight with respect to the weight of same cosmetic compositions;

and 8% to 20% of its weight of a system (S) formed by at least one anionic surfactant (TAn), at least one surfactant selected from betaines (TB) and at least one hydrosoluble or hydrodispersible cationic polymer derived from a polysaccharide (PolC);

the respective quantities of constituents (TAn), (TB) and (PolC) and the nature of the cationic polymer (PolC) in said system (S) being such that the transmittance of the aqueous phase (Φ) constituted by said system (S) in aqueous solution in a concentration of 8% to 20%, measured at 600 nanometres, is at least 90% and does not phase separate with formation of a precipitate on dilution, said aqueous phase (Φ), in the presence of said amphoteric surfactant (A), exhibiting phase separation behaviour with formation of a precipitate on dilution.

In order to implement the invention properly, said aqueous phase (Φ) comprises:
- of the order of 5% to 15% of its weight, preferably of the order of 8% to 12% of its weight, of at least one anionic surfactant (TAn);
- of the order of 0.5% to 10% of its weight, preferably of the order of 0.5% to 3% of its weight, of at least one surfactant selected from betaines (TB);
- and of the order of 0.015% to 2% of its weight, preferably of the order of 0.05% to 0.5% of its weight, of at least one cationic polymer (PolC).

Examples of cationic polymers (PolC), surfactants (TAn), (TB) and (A) which can be present in said compositions have already been described above.

The term "cosmetic composition or formulation" means all cosmetic products or preparations such as those described in annex I ("Illustrative list by category of cosmetic products") of European directive 76/768/EEC dated Jul. 27, 1976, known as the cosmetics directive.

The cosmetic compositions of the invention can be formulated into a large number of types of products for the skin and/or hair, gels (in particular styling gels), conditioners, formulations for styling or to facilitate combing the hair, rinsing formulae, body and hand lotions, products regulating skin hydration, toilet milks, make-up remover, shampoos, shower gels, liquid soaps and other compositions of similar type.

In a variation, said cosmetic compositions can also contain cosmetically interesting non hydrosoluble organic compounds (POins).

Said particles can be present in said compositions in an amount of the order of 0.1% to 10% by weight, preferably of the order of 0.2% to 2% by weight. They can be in the range 0.15 to 70 microns in size.

Examples of constituents (POins) which can be present in said compositions have already been mentioned.

To carry out the invention properly, the cosmetic compositions of the invention can also comprise fixative resins. These fixative resins are generally present in concentrations in the range 0.01 to 10%, preferably in the range 0.5% to 5%.

These fixative resins are preferably selected from methyl acrylate/acrylamide copolymers, polyvinylmethylether/maleic anhydride copolymers, vinyl acetate/crotonic acid copolymers, octylacrylamide/methyl acrylate/butylaminoethylmethacrylate copolymers, polyvinylpyrrolidones, polyvinylpyrrolidone/methyl methacrylate copolymers, polyvinylpyrrolidone/vinyl acetate copolymers, polyvinyl alcohols, polyvinyl alcohol/crotonic acid copolymers, polyvinyl alcohol/maleic anhydride copolymers, hydroxypropyl celluloses, hydroxypropyl guars, sodium polystyrene sulphonates, polyvinylpyrrolidone/ethyl methacrylate/methacrylic acid terpolymers, poly(methylvinylether/maleic anhydride) monomethyl ethers, polyvinyl acetates grafted onto polyoxyethylenated backbones (EP-A-0 219 048), copolyesters derived from terephthalic and/or isophthalic and/or sulphoisophthalic acid or anhydride or diester and a diol, such as:
- polyester copolymers based on ethylene terephthalate and/or propylene terephthalate and polyoxyethylene terephthalate motifs (U.S. Pat. No. 3,959,230, U.S. Pat. No. 3,893,929, U.S. Pat. No. 4,116,896, U.S. Pat. No. 4,702,857, U.S. Pat. No. 4,770,666);
- sulphonated polyester oligomers obtained by sulphonation of an oligomer derived from ethoxylated allyl alcohol, dimethylterephthalate and 1,2-propylene diol (U.S. Pat. No. 4,968,451);
- polyester copolymers based on propylene terephthalate and polyoxyethylene terephthalate motifs and terminated by ethyl or methyl motifs (U.S. Pat. No. 4,711,730) or polyester oligomers terminated by alkylpolyethoxy groups (U.S. Pat. No. 4,702,857) or anionic sulphopolyethoxy groups (U.S. Pat. No. 4,721,580), or sulphoaroyl groups (U.S. Pat. No. 4,877,896);
- polyester-polyurethanes obtained by reacting a polyester obtained from adipic acid and/or terephthalic acid and/or sulphoisophthalic acid and a diol, on a prepolymer with terminal isocyanate groups obtained from a polyoxyethylene glycol and a diisocyanate (FR-A-2 334 698);
- ethoxylated monoamines or polyamines, ethoxylated amine polymers (U.S. Pat. No. 4,597,898, EP-A-0 011 984);
- sulphonated polyester oligomers obtained by condensation of isophthalic acid, dimethyl sulphosuccinate and diethylene glycol (FR-A-2 236 926);
- polyester copolymers derived from dimethylterephthalate, isophthalic acid, dimethyl sulphoisophthalate and ethylene glycol (EP-A-0 540 374);
- copolymers comprising polyester units derived from dimethylterephthalate, isophthalic acid, dimethyl sulphoisophthalate and ethylene glycol and organopolysiloxane units (FR-A-2 728 915).

Preferably, the fixative resins are of the following types: polyvinylpyrrolidone (PVP), copolymers of polyvinylpyrrolidone and methyl methacrylate, copolymers of polyvinylpyrrolidone and vinyl acetate (VA), copolymers of ethylene glycol polyterephthalate and polyethylene glycol, copolymers of ethylene glycol polyterephthalate and polyethylene glycol and sodium polyisophthalate sulphonate, and mixtures thereof.

These fixative resins are preferably dispersed or dissolved in the selected vehicle.

The cosmetic compositions of the invention can also contain polymeric derivatives exerting a protective function.

These polymeric derivatives can be present in quantities of the order of 0.01–10%, preferably about 0.1–5%, and more particularly of the order of 0.2–3% by weight, for example:
- cellulose derivatives such as cellulose hydroxyethers, methyl cellulose, ethyl cellulose, hydroxypropyl methyl cellulose, hydroxybutyl methyl cellulose;
- polyvinyl esters grafted onto polyalkylene backbones such as polyvinylacetates grafted onto polyoxyethylenated backbones (EP-A-0 219 048);
- polyvinyl alcohols.

The performances of the cosmetic compositions of the invention can also be improved by using plasticisers. The plasticiser can constitute between 0.1% and 10% of the formulation, preferably 1% to 10%. Particularly suitable plasticisers which can be cited are adipates, phthalates, isophthalates, azelates, stearates, silicone copolyols, glycols, castor oil and mixtures thereof.

It is also advantageous to add metal sequestrating agents to these compositions, more particularly those sequestrating calcium, such as citrate ions.

It is also possible to incorporate moistening agents into the cosmetic compositions of the invention, such as glycerol, sorbitol, urea, collagen, gelatin, aloe vera or hyaluronic acid.

In order to further reduce irritation or damage to the scalp, it is also possible to add hydrosoluble or hydrodispersible polymers such as collagen or certain non allergenic derivatives of animal or vegetable proteins (wheat protein hydrolysates, for example), natural hydrocolloids (guar gum, carouba gum, tara gum . . . ) or from fermentation processes, and derivatives of these polycarbohydrates such as modified celluloses (for example hydroxyethylcellulose, carboxymethylcellulose), guar derivatives or carouba derivatives such as their non ionic derivatives (for example hydroxypropylguar), anionic derivatives (carboxymethylguar and carboxymethylhydroxypropylguar).

Preservatives such as methyl, ethyl, propyl and butyl esters of p-hydroxybenzoic acid, sodium benzoate, GERMABEN (trade name) or any chemical agent preventing bacterial or mould proliferation and traditionally used in cosmetic compositions are generally introduced into these compositions in an amount of 0.01% to 3% by weight. The quantity of these products is generally adjusted to avoid any proliferation of bacteria, mould or yeasts in the cosmetic compositions.

As an alternative to chemical agents, sometimes agents which modify the activity of water by greatly increasing the osmotic pressure can be used, such as carbohydrates or salts, can be used.

In general, in order to increase the pleasurable feel when the composition is used by the consumer, these ingredients have added to them one or more fragrances, colouring agents including those described in annex IV ("List of colouring agents allowed for use in cosmetic products") of European Directive 76/768/EEC dated Jul. 27, 1976, the Cosmetics Directive, and/or opacifying agents such as pigments. Fragrances, colouring agents or pigments can be added.

The composition can also contain viscosifying agents or gelling agents, such as cross-linked polyacrylates—CARBOPOL sold by GOODRICH, cellulose derivatives such as hydroxypropylcellulose, carboxymethylcellulose, guars and their derivatives, etc., used alone or in combination, or the same compounds, generally in the form of hydrosoluble polymers modified by hydrophobic groups covalently bonded to the polymer skeleton as described in International patent application WO-A-92/16187 and/or water to bring the total of the constituents of the formulation to 100%.

The cosmetic compositions of the invention can also contain polymeric dispersing agents in a quantity of the order of 0.1% to 7% by weight, to control the calcium and magnesium hardness, such as:

hydrosoluble salts of polycarboxylic acids with a molecular mass of the order of 2000 to 100000, obtained by polymerisation or copolymerisation of ethylenically unsaturated carboxylic acids such as acrylic acid, maleic acid or anhydride, fumaric acid, itaconic acid, aconitic acid, mesaconic acid, citraconic acid, methylenemalonic acid, and more particularly polyacrylates with a molecular mass of the order of 2000 to 10000 (U.S. Pat. No. 3,308,067), copolymers of acrylic acid and maleic anhydride with a molecular mass of the order of 5000 to 75000 (EP-A-0 066 915);

polyethylene glycols with a molecular mass of the order of 1000 to 50000.

The following examples are given by way of illustration.

EXAMPLE 1

The following formulations were prepared conventionally (final pH=6). The quantities are expressed as a percentage of active ingredient.

| Example 1 | | Formulation | | | | | |
|---|---|---|---|---|---|---|---|
| Ingredients | INCI name | 1 | 2 | 3 | 4 | 5 | 6 |
| Empicol ESB/3M (wt %) | Sodium lauryl ether sulphate (2EO) | 8 | 8 | 7 | 7 | 8 | 8 |
| Tegobetaine L7 (wt %) | Cocamidopropyl betaine | 2 | 2 | 2 | 2 | 0 | 0 |
| Miranol Ultra C32 (wt %) | Sodium cocoamphoacetate | 0 | 0 | 1 | 1 | 2 | 2 |
| Jaguar C162* (wt %) | Hydroxypropyl guar hydroxypropyl trimonium chloride | 0.3 | 0 | 0.3 | 0 | 0.3 | 0 |
| Jaguar C2000** (wt %) | Hydroxypropyl guar hydroxypropyl trimonium chloride | 0 | 0.3 | 0 | 0.3 | 0 | 0.3 |
| Water | | qsp 100 | qsp 100 | qsp 100 | qsp 100 | qsp 100 | qsp 100 |
| Transmittance (% at 600 nm) | | 100 | 100 | 100 | 100 | 100 | 100 |

*Jaguar C162: Hydroxypropyl guar hydroxypropyl trimonium chloride:
☐ hydroxypropyl group content: 0.6
☐ degree of substitution: 0.1
**Jaguar C2000: Hydroxypropyl guar hydroxypropyl trimonium chloride:
☐ hydroxypropyl group content: 0.6
☐ degree of substitution: 0.2

Formulations (formulae) 1 to 6 of the above table, containing about 10% by weight of dry matter, were diluted with increasing quantities of water: the transmittance of the diluted formulations was measured using a Jasco 7800 spectrophotometer.

Figure 1:
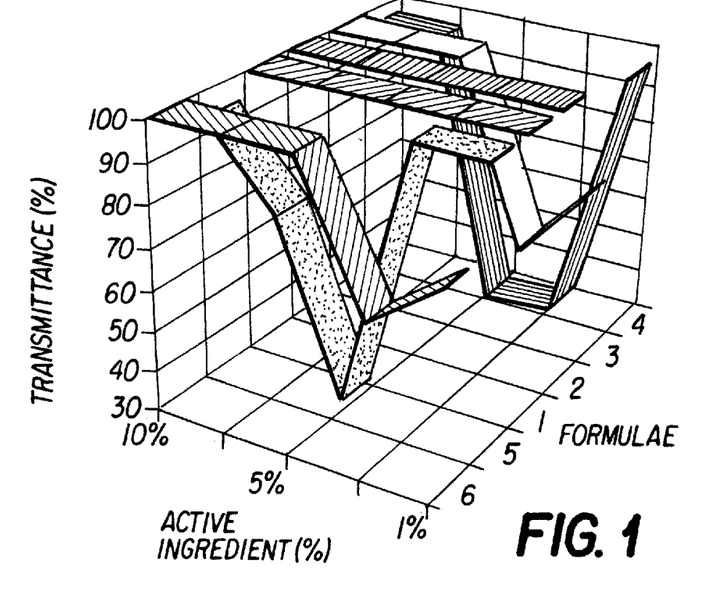
FIG. 1 is a graph showing the evolution of transmittance as a function of concentration of active ingredient in formulations of Example 1.

FIG. 1 shows the evolution of the transmittance as a function of the concentration of active ingredient.

It can be seen that the formulations containing the sodium cocoamphoacetate exhibited a precipitation phenomenon during dilution, while the formulations containing only cocamidopropyl betaine remained stable on dilution.

EXAMPLE 2

The following formulations were prepared conventionally (final pH=6). The quantities are expressed as a percentage of active ingredient.

| Example 2 | | Formulation | | | |
|---|---|---|---|---|---|
| Ingredients | INCI name | 1 | 3 | 7 | 5 |
| Empicol ESB/3M (wt %) | Sodium lauryl ether (2EO) sulphate | 8 | 7 | 7 | 8 |
| Tegobetaine L7 (wt %) | Cocamidopropyl betaine | 2 | 2 | 2 | 0 |
| Miranol CSE (wt %) | Sodium cocoampho hydroxypropyl sulphonate | 0 | 0 | 1 | 0 |
| Miranol Ultra C32 (wt %) | Sodium cocoamphoacetate | 0 | 1 | 0 | 2 |
| Jaguar C162 (wt %) | Hydroxypropyl guar hydroxypropyl trimonium chloride | 0.3 | 0.3 | 0.3 | 0.3 |
| | Transmittance (% at 600 nm) | 100 | 100 | 100 | 100 |

The formulations (formulae) of the above table, containing about 10% by weight of dry matter, were diluted with increasing quantities of water: the transmittance of the diluted formulations was measured using a Jasco 7800 spectrophotometer.

Figure 2:
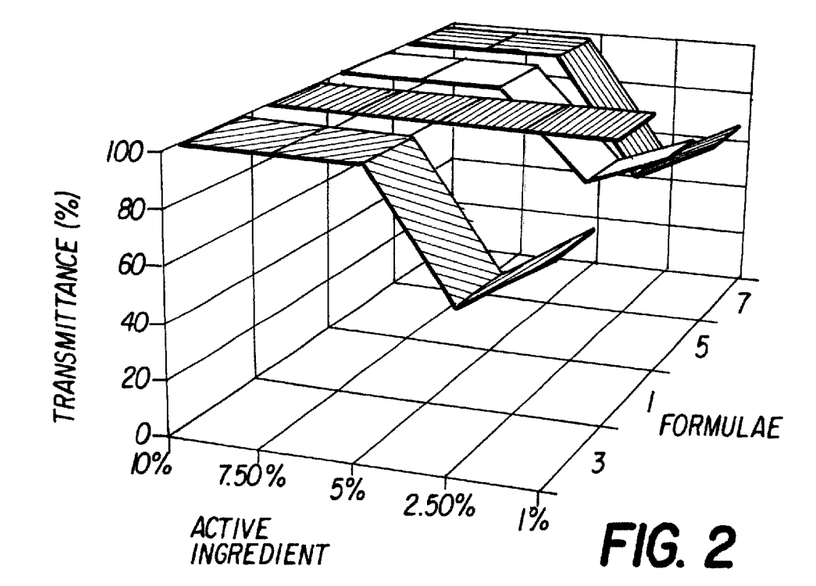
FIG. 2 is a graph showing the evolution of transmittance as a function of concentration of active ingredient in formulations of Example 2.

FIG. 2 shows the evolution of the transmittance as a function of the concentration of active ingredient.

Formulations containing the amphoteric surfactants exhibited a precipitation phenomenon during dilution. Formulations containing only cocamidopropyl betaine remained stable on dilution.

EXAMPLE 3

The following formulations were prepared conventionally (final pH=6). The quantities are expressed as a percentage of active ingredient.

| Example 3 | | Formulation | | | |
|---|---|---|---|---|---|
| Ingredients | INCI name | 3 | 8 | 9 | 1 |
| Empicol ESB/3M (wt %) | Sodium lauryl ether (2EO) sulphate | 7 | 7 | 8 | 8 |
| Tegobetaine L7 (wt %) | Cocamidopropyl betaine | 2 | 2 | 2 | 2 |
| Miranol Ultra C32 (wt %) | Sodium cocoamphoacetate | 1 | 1 | 0 | 0 |
| Jaguar C162 (wt %) | Hydroxypropyl guar hydroxypropyl trimonium chloride | 0.3 | 0 | 0.3 | 0 |
| Polymer JR 400 (cationic cellulose) (wt %) | Polyquaternium 10 | 0 | 0.3 | 0 | 0.3 |
| | Transmittance (% at 600 nm) | 100 | 100 | 100 | 100 |

The formulations (formulae) of the above table, containing about 10% by weight of dry matter, were diluted with increasing quantities of water: the transmittance of the diluted formulations was measured using a Jasco 7800 spectrophotometer.

Figure 3:
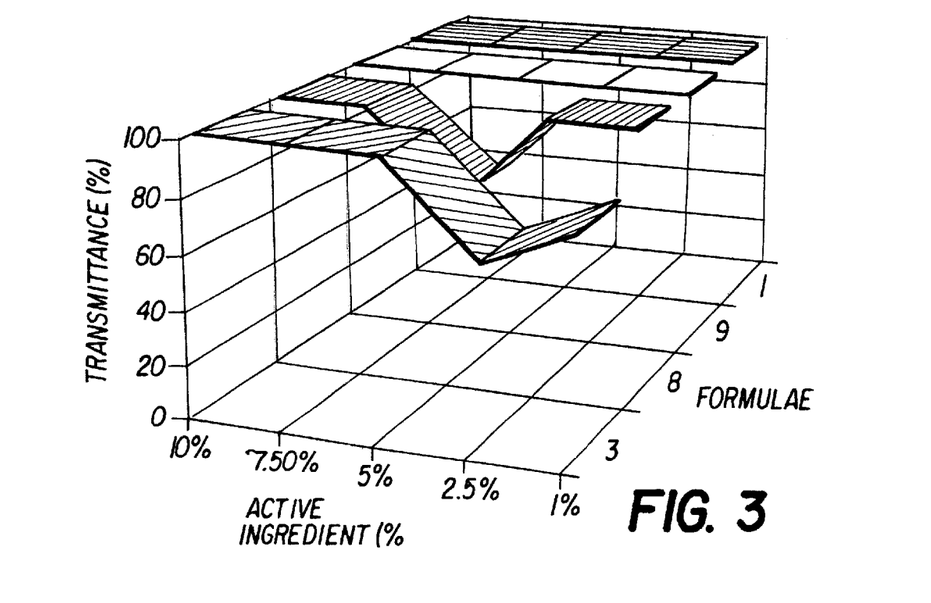
FIG. 3 is a graph showing the evolution of transmittance as a function of the concentration of active ingredient in formulations of Example 3.

FIG. 3 shows the evolution of transmittance as a function of the concentration of active ingredient.

The presence of amphoteric surfactant leads to precipitation phenomena during dilution.

EXAMPLE 4

Comparative (Non Hydroxyalkylated Cationic Guar)

The following formulations were prepared conventionally (final pH=6). The quantities are expressed as a percentage of active ingredient.

| Example 4 | | Formulation | | | |
|---|---|---|---|---|---|
| Ingredients | INCI name | 3 | 10 | 1 | 11 |
| Empicol ESB/3M (wt %) | Sodium lauryl ether sulphate (2EO) | 7 | 7 | 8 | 8 |
| Tegobetaine L7 (wt %) | Cocamidopropyl betaine | 2 | 2 | 2 | 2 |
| Miranol Ultra C32 (wt %) | Sodium cocoamphoacetate | 1 | 1 | 0 | 0 |
| Jaguar C162 (wt %) | Hydroxypropyl guar hydroxypropyl trimonium chloride | 0.3 | 0 | 0.3 | 0 |
| Jaguar C13S* (wt %) | Guar hydroxypropyl trimonium chloride | 0 | 0.3 | 0 | 0.3 |
| | Transmittance (% at 600 nm) | 100 | <70 | 100 | <70 |

*Jaguar C13S: Guar hydroxypropyl trimonium chloride:
☐ hydroxypropyl group content: 0
☐ degree of substitution: 0.1

Figure 4:
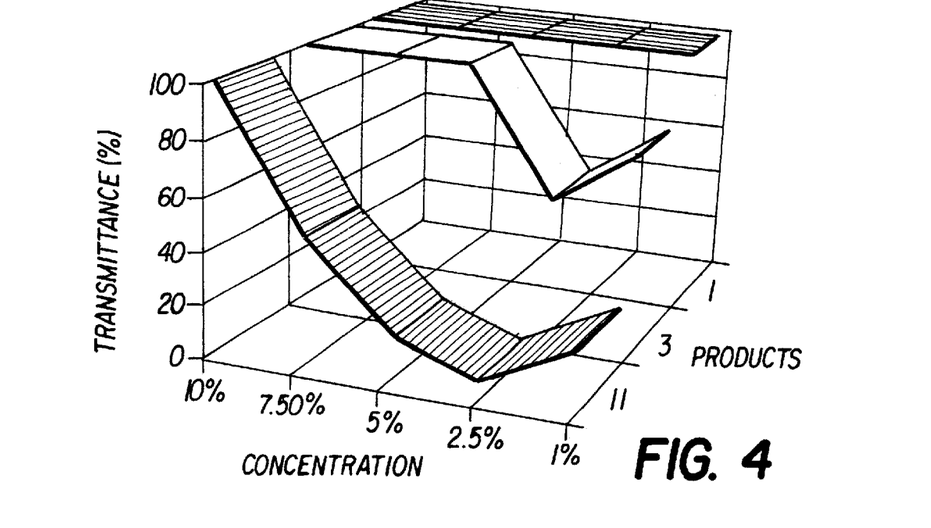
FIG. 4 is a graph showing the evolution of the transmittance as a function of the concentration of active ingredient in formulations of Comparative Example 4.

FIG. 4 shows the evolution of transmittance as a function of the concentration of active ingredient.

Formulation 11 containing a guar hydroxypropyl trimonium chloride (i.e., non hydroxyalkyenated) precipitated even in the absence of an amphoteric surfactant.

EXAMPLE 5

Comparative (Synthetic Non Polysaccharide Polymers)

The following formulations were prepared conventionally (final pH=6). The quantities are expressed as a percentage of active ingredient.

| Example 5 | | Formulation | | |
|---|---|---|---|---|
| Ingredients | INCI name | 3 | 12 | 13 |
| Empicol ESB/3M (wt %) | Sodium lauryl ether sulphate (2EO) | 7 | 7 | 7 |
| Tegobetaine L7 (wt %) | Cocamidopropyl betaine | 2 | 2 | 2 |
| Miranol Ultra C32 (wt %) | Sodium cocoamphoacetate | 1 | 1 | 1 |
| Jaguar C162 (wt %) | Hydroxypropyl guar hydroxypropyl trimonium chloride | 0.3 | 0 | 0 |
| Mirapol 550* (wt %) | Polyquaternium 7 | 0 | 0.3 | 0 |
| Mirapol A15** (wt %) | Polyquaternium 7 | 0 | 0 | 0.3 |
| | Transmittance (% at 600 nm) | 100 | 100 | 100 |

*Mirapol 550: obtained by polymerising acrylamide and dimethyldiallylammonium chloride.
**Mirapol A15: obtained by condensing urea bis(chloroethylether) and N,N-dimethylpropane diamine.

The formulations (formulae) of the above table, containing about 10% by weight of dry matter, were diluted with increasing quantities of water: the transmittance of the diluted formulations was measured using a Jasco 7800 spectrophotometer.

Figure 5:
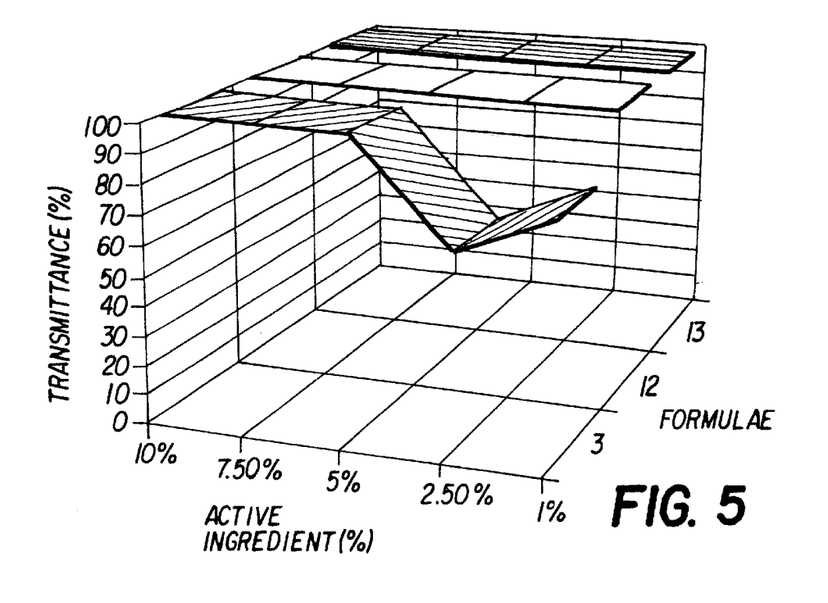
FIG. 5 is a graph showing the evolution of the transmittance as a function of the concentration of active ingredient in formulations of Comparative Example 5.

FIG. 5 shows the evolution of the transmittance as a function of the concentration of active ingredient.

It can be seen that the formulations containing Mirapol 550 and Mirapol A15, cationic polymers not derived from polysaccharides, did not precipitate on dilution.

EXAMPLE 6

Sensory Analysis

The following formulations were prepared conventionally (final pH=6). The quantities are expressed as a percentage of active ingredient.

| Example 6 | | Formulation | |
|---|---|---|---|
| Ingredients | INCI name | 1 | 3 |
| Empicol ESB/3M (wt %) | Sodium lauryl ether sulphate (2EO) | 8 | 7 |
| Tegobetaine L7 (wt %) | Cocamidopropyl betaine | 2 | 2 |
| Miranol Ultra C32 (wt %) | Sodium cocoamphoacetate | 0 | 1 |
| Jaguar C162 (wt %) | Hydroxypropyl guar hydroxypropyl trimonium chloride | 0.3 | 0.3 |
| Transmittance at 10% active (% at 600 nm) | | 100 | 100 |
| Transmittance at 2.5% active (% at 600 nm) | | 100 | 40 |

These formulations were evaluated by sensory analysis (panel of 25 judges).

Strands (European hair) of 7 were first pre-treated with a solution of lauryl sulphate (5%) for one hour. The strands were then rinsed with water and dried.

The strands were then washed with 0.7 g of formulation for 30 seconds, then rinsed for 45 seconds. The strands were then placed on rollers and dried. The results of the evaluation are summarized in FIG. 6.

Figure 6:
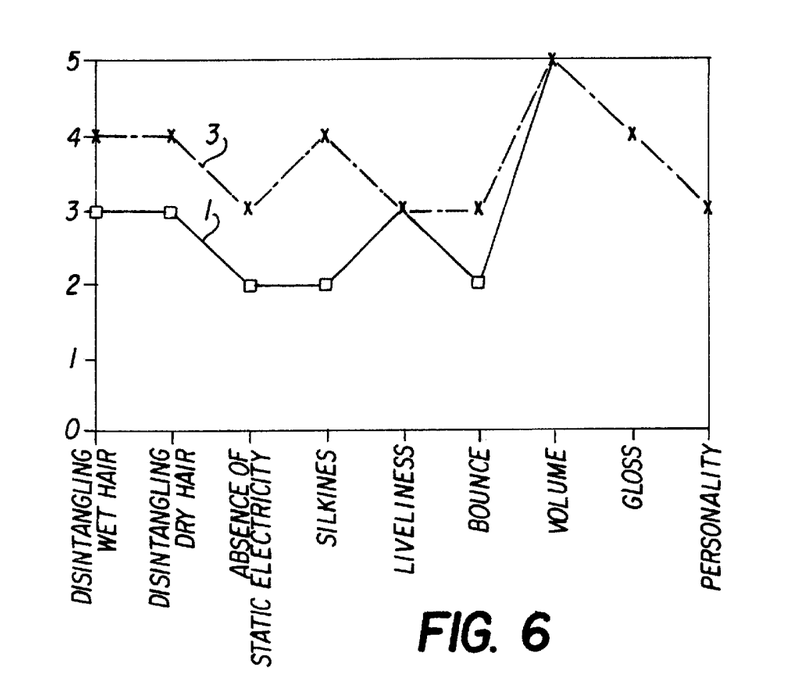
FIG. 6 is a graph of the sensory analysis of formulations of Example 6.

The phenomenon of controlled precipitation can improve disentangling, absence of static electricity and silkiness.

EXAMPLE 7

Increase of Deposit

The following formulations were prepared conventionally (final pH=6). The quantities are expressed as a percentage of active ingredient.

| Example 7 | | Formulation | |
|---|---|---|---|
| Ingredients | INCI name | 1 | 3 |
| Empicol ESB/3M (wt %) | Sodium lauryl ether sulphate (2EO) | 8 | 7 |
| Tegobetaine L7 (wt %) | Cocamidopropyl betaine | 2 | 2 |
| Miranol Ultra C32 (wt %) | Sodium cocoamphoacetate | 0 | 1 |
| Jaguar C162 (wt %) | Hydroxypropyl guar hydroxypropyl trimonium chloride | 0.3 | 0.3 |
| Rheozan (wt %) | Succinoglycan gum | 0.1 | 0.1 |
| Mirasil DME-30 (wt %) | Dimethicone emulsion (and) succinoglycan gum | 2 | 2 |

Strands of European hair (4 g) were first rinsed, then treated with a lauryl sulphate solution (10%) for 60 seconds. The strands were then rinsed for 60 seconds. This operation was repeated twice.

The strands were then washed with 0.25 g of formulation for 30 seconds, then rinsed for 60 seconds.

The strands were then dried in air for one hour.

The quantity of silicone deposited was measured after alcoholysis of the polymer deposited and measuring the volatile residues by gas chromatography.

The results are expressed as the deposit yield.

The deposit yield of formulation 1 was 4%; that of formulation 3 was 8%.

The presence of a small quantity of amphoteric surfactant thus enabled the quantity of silicone deposited on the hair to be doubled.

EXAMPLE 8

Shampoo and Conditioner

The quantities were expressed as the percentage of the product per se.

| Example 8 Ingredients | INCI name | Wt % |
|---|---|---|
| Empicol ESB/3M | Sodium lauryl ether sulphate | 25 |
| Tegobetaine L7 | Cocamidopropyl betaine | 6.7 |
| Miranol Ultra C32 | Sodium cocoamphoacetate | 3.2 |
| Jaguar C162 | Hydroxypropyl guar hydroxypropyl trimonium chloride | 0.3 |
| Citric acid | Citric acid | qs pH 6 |
| Fragrance | Fragrance | qs |
| Preservative | — | qs |
| Water | Aqua | qsp 100 |

Procedure

Disperse the Jaguar C162 in water and hydrate with citric acid. Add Miranol Ultra C32, Tegobetaine L7, then Empicol ESB3/M with stirring. Adjust the pH to 6.5 with citric acid.

EXAMPLE 9

Transparent Shower Gel

The quantities were expressed as the percentage of the product per se.

| Example 9 Ingredients | INCI name | Wt % |
|---|---|---|
| Jaguar C162 | Hydroxypropyl guar hydroxypropyl trimonium chloride | 0.2 |
| Mirasil ADM-E | Amodimethicone (and) trideceth-6 | 2 |
| Miranol Ultra C32 | Sodium cocoamphoacetate | 14 |

-continued

| Example 9 Ingredients | INCI name | Wt % |
|---|---|---|
| Empicol ESB/3M | Sodium lauryl ether sulphate | 34 |
| Mirataine CBS | Cocamidopropyl hydroxy sultaine | 3 |
| Preservative | — | Qs |
| Fragrance | Fragrance | 0.2 |
| Tween 20 | Polysorbate 20 | 0.2 |
| Citric acid | Citric acid | 2.3 |
| Sodium chloride | Sodium chloride | qs |
| Water | Aqua | qs 100 |

Procedure

Disperse the Jaguar C162 in water and hydrate with citric acid. Add the other ingredients in the order indicated, with stirring. Adjust the pH to 6.5 with citric acid.

EXAMPLE 10

Shower Gel

The quantities were expressed as the percentage of the product per se.

| Example 10 Ingredients | INCI name | Wt % |
|---|---|---|
| Empicol ESB/3M | Sodium lauryl ether sulphate | 25 |
| Tegobetaine L7 | Cocamidopropyl betaine | 6.7 |
| Miranol CSE | Sodium cocoampho hydroxypropyl sulphonate | 3.2 |
| Polymer JR400 | Polyquaternium-10 | 0.3 |
| Citric acid | Citric acid | qs pH 6 |
| Fragrance | Fragrance | qs |
| Preservative | — | qs |
| Water | Aqua | qsp 100 |

Procedure

Disperse the Polymer JR400 in water and add the Miranol CSE, Tegobetaine L7, then Empicol ESB3/M with stirring. Adjust the pH to 6.5 with citric acid.

What is claimed is:

1. A transparent aqueous cosmetic composition for the hair or skin, intended to be rinsed, comprising:
    at least one amphoteric surfactant in a quantity of about 0.5% to 10% by weight, with respect to the weight of said cosmetic composition, as an agent for precipitating a hydrosoluble or hydrodispersible hydroxyalkylated cationic guar derivative on dilution during application of said composition to the hair or skin, and
    at least 90% of the weight of said transparent aqueous cosmetic composition comprising an aqueous phase whose 8% to 20% of its weight being a system formed by at least one anionic surfactant, at least one surfactant selected from the group consisting of betaines and at least one hydrosoluble or hydrodispersible hydroxyalkylated cationic guar derivative; wherein the aqueous phase is constituted by said system in aqueous solution in a concentration of 8% to 20%, presents a transmittance, measured at 600 nanometers, of at least 90%, and does not phase separate with formation of a precipitate on dilution, and wherein said aqueous phase exhibits phase separation behavior with formation of a precipitate on dilution in the presence of said amphoteric surfactant.

2. A cosmetic composition according to claim 1, wherein the quantity of amphoteric surfactant is of about 0.5% to 3%.

3. A cosmetic composition according to claim 1, wherein said aqueous phase comprises:
    about 5% to 15% of its weight, of at least one anionic surfactant;
    about 0.5% to 10% of its weight, of at least one surfactant selected from betaines; and
    about 0.015% to 2% of its weight of at least one hydroxyalkylated cationic guar derivative.

4. A cosmetic composition according to claim 3, wherein said aqueous phase comprises:
    about 8% to 12% of its weight, of at least one anionic surfactant;
    about 0.5% to 3% of its weight, of at least one surfactant selected from betaines; and
    about 0.05% to 0.5% of its weight, of at least one hydroxyalkylated cationic guar derivative.

5. A cosmetic composition according to claim 1, wherein said hydroxyalkylated cationic guar derivative is hydroxypropyl guar hydroxypropyltrimonium chloride.

6. A cosmetic composition according to claim 1, wherein said anionic surfactant is an alkylester sulphonate, alkylsulphate, ethoxylenated alkylsulphate, propoxylenated alkylsulphate, alkylamide sulphate, ethoxylenated alkylamide sulphate, propoxylenated alkylamide sulphate, salt of saturated fatty acid, or salt of unsaturated fatty acid.

7. A cosmetic composition according to claim 4, wherein said surfactant is betaine, sulphobetaine, or amidoalkylbetaine.

8. A cosmetic composition according to claim 1, wherein said amphoteric surfactant is an alkyl-amphoacetate, alkenyl-amphoacetate, amphodiacetate, alkylamphopropionate, alkylampho-dipropionate, or alkylamphohydroxypropyl sultaine, wherein the alkyl groups contain 8 to 24 carbon atoms.

9. A cosmetic composition according to claim 1, wherein said amphoteric surfactant further contains at least one non hydrosoluble organic compound as an agent for precipitating said hydroxyalkylated cationic guar derivative and as an agent for depositing particles of said non hydrosoluble organic compound on dilution.

10. A cosmetic composition according to claim 9, wherein the non hydrosoluble organic compound is present in an amount of 0.1% to 10%.

11. A cosmetic composition according to claim 10, wherein said amount is of 0.2% to 2% by weight.

12. A cosmetic composition according to claim 10, wherein said non hydrosoluble organic compound is a non hydrosoluble and non volatile organopolysiloxane, an oil exerting a conditioning, protective or emollient function, a bactericidal agent, a fungicidal agent, or a sun screen.

13. A cosmetic composition according to claim 1, further comprising at least one additive selected from the group consisting of a fixative resin, polymer exerting a protective action, plasticiser, metal sequestrating agent, moistening agent, hydrosoluble polymer, hydrodispersible polymer, preservative, fragrance, coloring agent, pigment, viscosifying polymer, gelling polymer, and polymeric dispersing agent.

* * * * *